(12) United States Patent
Kawashima et al.

(10) Patent No.: US 6,984,673 B2
(45) Date of Patent: Jan. 10, 2006

(54) DENTAL CEMENT COMPOSITION

(75) Inventors: Mitsunobu Kawashima, Kurashiki (JP); Ikuo Omura, Kurashiki (JP); Mayumi Yamashita, Kurashiki (JP)

(73) Assignee: Kuraray Co., Ltd., Kurashiki (JP)

( * ) Notice: Subject to any disclaimer, the term of this patent is extended or adjusted under 35 U.S.C. 154(b) by 408 days.

(21) Appl. No.: 10/183,515

(22) Filed: Jun. 28, 2002

(65) Prior Publication Data

US 2003/0055123 A1    Mar. 20, 2003

(30) Foreign Application Priority Data

Jun. 28, 2001    (JP) .............................. 2001-195704

(51) Int. Cl.
*A61K 6/08* (2006.01)
*A61F 6/00* (2006.01)

(52) U.S. Cl. ...................... 523/116; 523/115; 523/118; 523/120; 524/435; 526/277; 433/228.1

(58) Field of Classification Search ................ 523/115, 523/116, 118; 524/535; 526/277; 106/35; 433/228.1

See application file for complete search history.

(56) References Cited

U.S. PATENT DOCUMENTS

| 4,182,035 A | 1/1980 | Yamauchi et al. |
| 4,539,382 A | 9/1985 | Omura et al. |
| 4,816,495 A | 3/1989 | Blackwell et al. |
| 4,966,934 A * | 10/1990 | Huang et al. ................ 524/315 |
| 5,063,257 A | 11/1991 | Akahane et al. |
| 5,130,347 A | 7/1992 | Mitra |
| 5,367,002 A | 11/1994 | Huang et al. |
| 5,520,725 A | 5/1996 | Kato et al. |
| 5,760,101 A | 6/1998 | Heiliger et al. |
| 5,808,104 A | 9/1998 | Podszun et al. |

FOREIGN PATENT DOCUMENTS

| JP | 2-6358 | 1/1990 |
| JP | 2-164807 | 6/1990 |
| JP | 5-255033 | 10/1993 |
| JP | 8-26925 | 1/1996 |
| JP | 10-505868 | 6/1998 |
| JP | 10-506127 | 6/1998 |

OTHER PUBLICATIONS

Patent Abstracts of Japan, JP 2000-026225, Jan. 25, 2000.
Patent Abstracts of Japan, JP 09-249514, Sep. 22, 1997.
I. A. Mjör, The Quintessence, vol. 16, No. 4, pp. 69-72, "Glass-Ionomer Cement Restorations and Secondary Caries: A Preliminary Report", 1997 (with English version, Quintessence International, vol. 27, Iss. 3, pp. 171-174, Mar. 1996).

* cited by examiner

Primary Examiner—Tae H. Yoon
(74) Attorney, Agent, or Firm—Oblon, Spivak, McClelland, Maier & Neustadt, P.C.

(57) ABSTRACT

One embodiment of the invention provides a dental cement composition which includes (a) an acid group-having polymerizable monomer, (b) a polyalkenoic acid, (c) an ion-leachable glass filler, (d) a polymerizable monomer not having an acid group, (e) water, (f) a peroxide, (g) a salt of an aromatic sulfinic acid, and (h) an aromatic secondary amine and/or an aromatic tertiary amine.

33 Claims, No Drawings

DENTAL CEMENT COMPOSITION

BACKGROUND OF THE INVENTION

1. Field of the Invention

The present invention relates to a dental cement composition. Precisely, the invention relates to a dental cement composition, which, after being cured, is stable and bonds well to hard tissues such as tooth enamel and dentin and to prostheses such as inlays, onlays, crowns, cores, posts and bridges that are formed of metals, porcelains, ceramics and composite resins, and which is therefore useful in restoring decayed or injured teeth and in bonding prostheses.

2. Discussion of the Background

Amalgam, glass ionomer cement and composite resin are widely used for restoring decayed or injured teeth. On the other hand, zinc phosphate cement, glass ionomer cement and composite resin cement for bonding prostheses such as crowns, inlays and bridges to decayed or injured teeth. In that manner, various materials are used for restoring decayed or injured teeth, and one of them is glass ionomer cement.

The basic components of glass ionomer cement are a polyalkenoic acid, water and an ion-leachable glass filler. Attempts to improve the properties of glass ionomer cement, by adding other components, for example, are described in Japanese Patent Laid-Open Nos. 164807/1990, 6358/1990, 255033/1993, 26925/1996, and International Patent Publication Nos. 505868/1998, 506127/1998. The improved glass ionomer cements described therein are generally referred to as resin-modified glass ionomer cements, and which become popular in the art.

The basic principle in the restoration of defective teeth is to fill an aesthetic material having a certain strength in the cavity of a defective tooth or in the space between defective teeth and a prosthesis to ensure the permanence of the restored teeth, not to merely improve the function and shape of the restored teeth temporarily. Another purpose is to prevent the recurrence of caries.

In general, it is known that glass ionomer cement releases fluorine, which is effective for making teeth acid resistant from the viewpoint of caries prevention, but the fluorine release is only an auxiliary function of the glass ionomer cement. Specifically, if the cause of secondary caries is not eliminated, fluorine release, if any, to reinforce teeth could not be the essential solution to the problem of caries. To solve the problem of caries, it is first necessary to seal the interface between a restored tooth and a prosthesis with cement. This is to prevent caries-causing bacteria from invading the aforesaid interface and to prevent food residues that may provide the nutrients for the bacteria from entering, to thereby prevent secondary caries from recurring.

The function of fluorine may be taken into consideration merely as an auxiliary preventive means for bonding failure in the restored tooth. As reported in *Quintessence*, Vol. 16, No. 4 (1997), pp. 69–72, secondary caries accounts for about 50% of the reason for re-restoration of teeth once restored with glass ionomer cement, and is significant. This is because of mistaking the means for the end in that fluorine only is expected for caries prevention.

The oral environment to which tooth restorations are exposed is described. The oral cavity is always wetted with saliva circulating therein, and it is well known that, when plaque adheres to teeth, the area around the tooth becomes acidic owing to the acid produced by the bacteria in the plaque. Some food is acidic by itself. The oral temperature is generally equal to body temperature and is around 37° C., but this varies from around 0° C. to about 60° C. depending on the food taken. This means that teeth are exposed to heat shock. In addition, teeth receive some mechanical stress while they meet or while food is chewed. To that effect, tooth restorations are always in such extremely severe conditions. In the oral cavity that is generally in such a wet and acidic condition, glass ionomer cement will disintegrate, and the disintegration of the cement itself is a problem to be discussed before the bonding power of the cement to teeth and prostheses to seal decayed teeth are discussed.

Accordingly, it is a matter of first importance to prevent the cement disintegration in that condition. In addition, increasing the bonding power of the cement in the bonding interface will achieve tooth restorations of a higher level. However, conventional resin-modified glass ionomer cement do not fully solve the problems.

SUMMARY OF THE INVENTION

We, the present inventors have assiduously studied to solve the problems noted above, and, as a result, have found that a glass ionomer cement composition that includes specific ingredients disintegrates little in the oral cavity and bonds well to hard tissues such as tooth enamel and dentin and to prostheses formed of various materials. On the basis of this finding, we have completed the present invention.

Accordingly, one embodiment of the invention provides a dental cement composition, which includes (a) an acid group-having polymerizable monomer, (b) a polyalkenoic acid, (c) an ion-leachable glass filler, (d) a polymerizable monomer not having an acid group, (e) water, (f) a peroxide, (g) a salt of an aromatic sulfinic acid, and (h) an aromatic secondary amine and/or an aromatic tertiary amine.

Another embodiment of the invention provides a method, which includes introducing the above-mentioned composition into the oral cavity of a subject.

Another embodiment of the invention provides a method, which includes contacting the above-mentioned composition with at least one selected from the group including hard tissue, tooth enamel, dentin, prosthesis, inlay, onlay, crown, core, post, bridge, metal, porcelain, ceramic, composite resin, and combinations thereof.

Another embodiment of the invention provides a dental cement, which includes a cured product of the above-mentioned composition.

Another embodiment of the invention provides a dental applicance or article, which includes a cured product of the above-mentioned composition in contact with at least one selected from the group including hard tissue, tooth enamel, dentin, prosthesis, inlay, onlay, crown, core, post, bridge, metal, porcelain, ceramic, composite resin, and combinations thereof.

Another embodiment of the invention provides a dental cement composition kit, which includes:

(A) a liquid composition, which includes:
  (a) an acid group-having polymerizable monomer,
  (b) a polyalkenoic acid,
  (d) a polymerizable monomer not having an acid group,
  (e) water, and
  (f) a peroxide; and (B) a powdery composition, which includes:
  (c) an ion-leachable glass filler,
  (g) a salt of an aromatic sulfinic acid, and
  (h) at least one selected from the group including an aromatic secondary amine, an aromatic tertiary amine, and a combination thereof;

wherein (A) and (B) are packaged separately from each other.

Another embodiment of the invention provides a method for making a dental cement, which includes contacting components (A) and (B).

Another embodiment of the invention provides a method, which includes introducing components (A) and (B), or a mixture thereof, into the oral cavity of a subject.

Another embodiment of the invention provides a method, which includes contacting components (A) and (B), or a mixture thereof, with at least one selected from the group including hard tissue, tooth enamel, dentin, prosthesis, inlay, onlay, crown, core, post, bridge, metal, porcelain, ceramic, composite resin, and combinations thereof.

Another embodiment of the invention provides a dental cement, which includes a cured product of components (A) and (B).

Another embodiment of the invention provides a dental appliance or article, which includes a cured product of the components (A) and (B) in contact with at least one selected from the group including hard tissue, tooth enamel, dentin, prosthesis, inlay, onlay, crown, core, post, bridge, metal, porcelain, ceramic, composite resin, and combinations thereof.

Another embodiment of the invention provides a dental cement composition kit, which includes:
(C) a paste composition, which includes:
  (a) an acid group-having polymerizable monomer,
  (b) a polyalkenoic acid,
  (d) a polymerizable monomer not having an acid group,
  (e) water,
  (f) a peroxide, and
  (i) a non-leachable filler; and
(D) a paste composition, which includes:
  (c) an ion-leachable glass filler,
  (d) a polymerizable monomer not having an acid group,
  (g) a salt of an aromatic sulfinic acid, and
  (h) at least one selected from the group including an aromatic secondary amine, an aromatic tertiary amine, and a combination thereof;
wherein (C) and (D) are packaged separately from each other.

Another embodiment of the invention provides a method for making a dental cement, which includes contacting components (C) and (D).

Another embodiment of the invention provides a method, which includes introducing components (C) and (D), or a mixture thereof, into the oral cavity of a subject.

Another embodiment of the invention provides a method, which includes contacting components (C) and (D), or a mixture thereof, with at least one selected from the group including hard tissue, tooth enamel, dentin, prosthesis, inlay, onlay, crown, core, post, bridge, metal, porcelain, ceramic, composite resin, and combinations thereof.

Another embodiment of the invention provides a dental cement, which includes a cured product of components (C) and (D).

Another embodiment of the invention provides a dental appliance or article, which includes a cured product of the components (C) and (D) in contact with at least one selected from the group including hard tissue, tooth enamel, dentin, prosthesis, inlay, onlay, crown, core, post, bridge, metal, porcelain, ceramic, composite resin, and combinations thereof.

Another embodiment of the invention provides a method for making a dental cement, which includes contacting the following components (a) to (h) and curing:
(a) an acid group-having polymerizable monomer,
(b) a polyalkenoic acid,
(c) an ion-leachable glass filler,
(d) a polymerizable monomer not having an acid group,
(e) water,
(f) a peroxide,
(g) a salt of an aromatic sulfinic acid,
and (h) at least one selected from the group including an aromatic secondary amine, an aromatic tertiary amine, and a combination thereof.

Surprisingly and unexpectedly, the dental cement composition of the invention disintegrates little in the oral cavity and bonds well to teeth and prostheses, and it is therefore particularly useful in restoring decayed or injured teeth.

DESCRIPTION OF THE PREFERRED EMBODIMENTS

Various other objects, features and attendant advantages of the present invention will be more fully appreciated as the same becomes better understood from the following detailed description.

The acid group-having polymerizable monomer (a) in the dental cement composition of the invention is indispensable for ensuring the bonding power of the cement composition to teeth. The polymerizable monomer has at least one acid group of, for example, a phosphoric acid group, pyrophosphoric acid group, carboxylic acid group, sulfonic acid group or thiophosphoric acid group, and has a polymerizable unsaturated group such as an acryloyl group, methacryloyl group, vinyl group or styrene group. Combinations are possible.

Preferred examples of the (a) compounds are mentioned below. (Meth)acryl is meant to include methacryl and acryl. Examples of the phosphoric acid group-having polymerizable monomers are 2-(meth)acryloyloxyethyl dihydrogen phosphate, 3-(meth)-acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicoscyl dihydrogen phosphate, di(2-(meth)acryloyloxyethyl) hydrogen phosphate, di(4-(meth)acryloyloxybutyl) hydrogen phosphate, di(6-(meth)acryloyloxyhexyl) hydrogen phosphate, di(8-(meth)acryloyloxyoctyl) hydrogen phosphate, di(9-(meth)acryloyloxynonyl) hydrogen phosphate, di(10-(meth)acryloyloxydecyl) hydrogen phosphate, 1,3-di(meth)acryloyloxypropyl)-2-dihydrogen phosphate, 2-(meth)acryloyloxyethyl phenyl hydrogen phosphate, 2-(meth)acryloyloxyethyl phenyl-2'-bromoethyl hydrogen phosphate, 2-(meth)acryloyloxyethyl phenyl phosphonate (5-methacryloxy)pentyl-3-phosphonopropionate, (6-methacryloxy)hexyl-3-phosphonopropionate, (10-methacryloxy)decyl-3-phosphonopropionate, (6-methacryloxy)hexyl-3-phosphonoacetate, (10-methacryloxy)decyl-3-phosphonoacetate, 2-methacryloyloxyethyl-4-ethoxyphenyl hydrogen phosphate, 2-methacryloyloxypropyl-4-ethoxyphenyl hydrogen phosphate, glycerol phosphate di(meth)acrylate, dipentaerythritol phosphate penta(meth)acrylate; and their acid chlorides. Combinations are possible.

Preferred examples of the pyrophosphoric acid-having polymerizable monomers are di(2-(meth)acryloyloxyethyl) pyrophosphate, di(4-(meth)acryloyloxybutyl) pyrophosphate, di(6-(meth)acryloyloxyhexyl) pyrophosphate, di(8-(meth)acryloyloxyoctyl) pyrophosphate, di(10-(meth)acryloyloxydecyl) pyrophosphate; and their acid chlorides. Combinations are possible.

Preferred examples of the carboxylic acid group-having polymerizable monomers are maleic acid, methacrylic acid, 4-((meth)acryloyloxyethoxycarbonyl)phthalic acid, 4 ((meth)acryloyloxybutyloxycarbonyl)phthalic acid, 4-((meth)acryloyloxyhexyloxycarbonyl)phthalic acid, 4-((meth)acryloyloxyoctyloxycarbonyl)phthalic acid, 4-((meth)acryloyloxydecyloxycarbonyl)phthalic acid, and their acid anhydrides; 5-(meth)acryloylaminopentylcarboxylic acid, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, 11-(meth) acryloyloxy-1,1-undecanedicarboxylic acid; and their acid chlorides. Combinations are possible.

Preferred examples of the sulfonic acid group-having polymerizable monomers are 2-(meth)acrylamido-2-methylpropanesulfonic acid, styrenesulfonic acid, 2-sulfoethyl (meth)acrylate; and their acid chlorides. Combinations are possible.

Preferred examples of the thiophosphoric acid group-having polymerizable monomers are 10-(meth)acryloyloxydecyl dihydrogen dithiophosphate and its acid chlorides. Combinations are possible.

Of those acid group-having polymerizable monomers, more preferred are phosphoric acid or thiophosphoric acid group having polymerizable monomers as the cement composition containing the monomer of the type bonds particularly well to teeth and prostheses. More especially preferred are polymerizable monomers of the following formula (I); and even more particularly preferred are those of the following formulas (II) and/or (III).

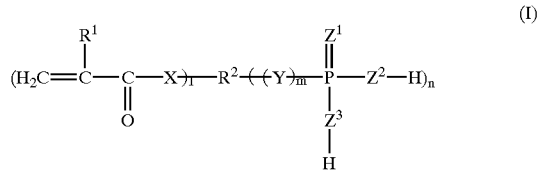
(I)

wherein $R^1$ represents a hydrogen atom or a methyl group; $R^2$ represents an organic group having from 2 to 40 carbon atoms; X represents a group of —O— or —NH—; l indicates an integer of 1, 2, 3, 4 or 5; m indicates an integer of 0 or 1; n indicates an integer of 1, 2, 3 or 4; Y represents a group of —O— or —S—; and $Z^1$, $Z^2$ and $Z^3$ each independently represents an oxygen atom or a sulfur atom.

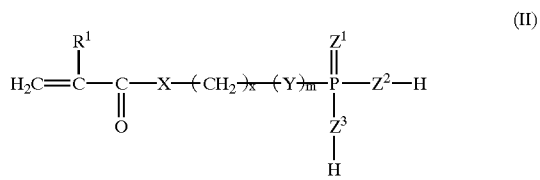
(II)

wherein $R^1$ represents a hydrogen atom or a methyl group; X represents a group of —O— or —NH—; x indicates an integer of 4, 5, 6, 7, 8, 9, 10, 11, 12, 13, 14, 15, 16, 17, 18, 19 or 20; m indicates an integer of 0 or 1; Y represents a group of —O— or —S—; and $Z^1$, $Z^2$ and $Z^3$ each independently represents an oxygen atom or a sulfur atom.

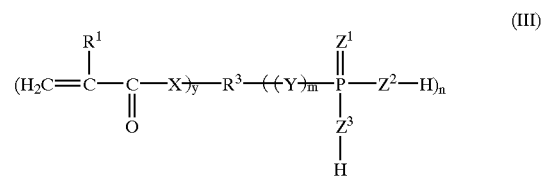
(III)

wherein $R^1$ represents a hydrogen atom or a methyl group; $R^3$ represents an organic group having 3, 4, 5, 6, 7, 8, 9, or 10 carbon atoms; X represents a group of —O— or —NH—; y indicates an integer of 2, 3, 4, or 5; m indicates an integer of 0 or 1; n indicates an integer of 1, 2, 3 or 4; Y represents a group of —O— or —S—; and $Z^1$, $Z^2$ and $Z^3$ each independently represents an oxygen atom or a sulfur atom.

In formula (I), $R^2$ represents an organic group having 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 carbon atoms, and is preferably an alkyl group having 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 carbon atoms. In formula (III), $R^3$ represents an organic group having from 3, 4, 5, 6, 7, 8, 9 or 10 carbon atoms, and is preferably an alkyl group having from 3 to 10 carbon atoms.

The term "organic group" herein preferably includes a straight or branched alkyl group, aryl group or aralkyl group.

The polyalkenoic acid (b) for use in the invention is an organic polymer having a carboxyl group or any other acid group capable of reacting with the cation released by the ion-leachable glass filler (c) to form a poly-salt. The filler (c) is described in detail hereinunder. Preferably, the acid (b) is a polymer of an unsaturated monocarboxylic acid or an unsaturated dicarboxylic acid, including, for example, homopolymers of acrylic acid, methacrylic acid, 2-chloroacrylic acid, 2-cyanoacrylic acid, aconitic acid, mesaconic acid, maleic acid, itaconic acid, fumaric acid, glutaconic acid or citraconic acid, and copolymers of such unsaturated carboxylic acids with other comonomers. Combinations are possible. In the copolymers, the proportion of the unsaturated carboxylic acid units is preferably at least 50 mol % to the total constitutive units. The comonomers are preferably ethylenic unsaturated polymerizable comonomers, including, for example, styrene, acrylamide, acrylonitrile, methyl methacrylate, salts of acrylic acid, vinyl chloride, allyl chloride, vinyl acetate, 1,1,6-trimethylhexamethylene dimethacrylate. Of those polyalkenoic acids, preferred are homopolymers and copolymers of acrylic acid or maleic acid.

If the weight-average molecular weight of the polyalkenoic acid is not higher than 5,000, the strength of the cured product of the cement composition containing the acid will be low and the durability thereof will be poor. On the other hand, if the weight-average molecular weight of the polyalkenoic acid is higher than 40,000, the viscosity of the cement composition containing the acid will be too high to manipulate the cement composition in clinical practice, and the workability thereof will be poor. Accordingly, it is desirable that the polyalkenoic acid has a weight-average molecular weight of from 5,000 to 40,000. This range includes all values and subranges therebetween, including 6,000, 8,000, 10,000, 20,000, and 30,000.

The ion-leachable glass filler (c) for use in the invention releases divalent or more polyvalent cations of, for example, strontium, calcium, zinc, aluminum, iron or zirconium capable of reacting with the polyalkenoic acid (b). Preferably, it includes, for example, one or more of fluoroaluminosilicate glass, calcium fluoroaluminosilicate glass, strontium fluoroaluminosilicate glass, barium fluoroaluminosilicate glass, and strontium calcium fluoroaluminosilicate glass. Of those, more preferred are fluoroaluminosilicate glass and barium fluoroaluminosilicate glass.

If the mean particle size of the ion-leachable glass filler is larger than 20 μm, the surface of the cured product of the cement composition containing the filler of such coarse particles will be roughened and will therefore has a rough feel, and, in addition, the workability of the cement composition will be poor. On the other hand, if the mean particle size of the ion-leachable glass filler is smaller than 0.02 μm, the amount of the filler of such fine particles that may be mixed with other liquid ingredients to formulate cement compositions will be low and, if so, the physical properties of the cement composition containing the filler of such fine particles will be not good. Accordingly, it is desirable that the ion-leachable glass filler has a mean particle size of from 0.02 to 20 μm. This range includes all values and subranges therebetween, including 0.05, 0.1, 0.5, 0.9, 1.0, 2, 4, 6, 8, 10, 12, 14, 16 and 18 μm.

Preferably, the ion-leachable glass filler (c) may be previously surface-treated with any known surface-treating agent such as a silane coupling agent. The surface-treating agent includes, for example, vinyltrimethoxysilane, vinyltriethoxysilane, vinyltrichlorosilane, vinyltri(β-methoxyethoxy)silane, γ-methacryloylpropyltrimethoxysilane, γ-glycidoxypropyltrimethoxysilane, γ-mercaptopropyltrimethoxysilane, γ-aminopropyltriethoxysilane. Combinations are possible.

The polymerizable monomer (d) not having an acid group, which is in the dental cement composition of the invention, includes, for example, esters such as α-cyanoacrylates, (meth)acrylates, α-halogenoacrylates, crotonates, cinnamates, sorbates, maleates, itaconates; and (meth) acrylamide derivatives, vinyl esters, vinyl ethers, mono-N-vinyl derivatives, styrene derivatives. Combinations are possible. Of those, preferred are (meth)acrylates.

Examples of the polymerizable monomer (d) not having an acid group for use in the invention are mentioned below. Monomers having one olefinic double bound in the molecule are referred to as monofunctional monomers; and those having two or more olefinic double bonds in the molecule are referred to as difunctional, trifunctional or more polyfunctional monomers depending on the number of the olefinic double bonds therein.

Monofunctional Monomers:

Methyl (meth)acrylate, ethyl (meth)acrylate, propyl (meth)acrylate, isopropyl (meth)acrylate, butyl (meth)acrylate, isobutyl (meth)acrylate, benzyl (meth)acrylate, lauryl (meth)acrylate, 2,3-dibromopropyl (meth)acrylate, 2-hydroxyethyl (meth)acrylate, 2-hydroxypropyl (meth) acrylate, 3-hydroxypropyl (meth) acrylate, 1,3-dihydroxypropyl (meth)acrylate, 2,3-dihydroxypropyl (meth)acrylate, 2-hydroxyethyl(meth)acrylamide, 3-methacryloyloxypropyltrimethoxysilane, 11-methacryloyloxyundecyltrimethoxysilane, (meth)acrylamide. Combinations are possible.

Difunctional Monomers:

Ethylene glycol di(meth)acrylate, triethylene glycol di(meth)acrylate, propylene glycol di(meth)acrylate, polyethylene glycol di(meth)acrylates (having at least 9 oxyethylene groups), neopentyl glycol di(meth)acrylate, 1,6-hexanediol di(meth)acrylate, 1,10-decanediol di(meth)acrylate, dipentaerythritol di(meth)acrylate, 2,2-bis(4-(meth)acryloyloxy-ethoxyphenyl)propane, 2,2-bis(4-(meth)acryloyloxypolyethoxyphenyl)propane, 2,2-bis(4-(3-(meth)acryloyloxy-2-hydroxypropoxy)phenyl)-propane, 1,2-bis(3-(meth) acryloyloxy-2-hydroxypropoxy)ethane, pentaerythritol di(meth)acrylate, 1,2-bis(3-methacryloyloxy-2-hydroxypropoxy)ethane, (2,2,4-trimethylhexamethylenebis(2-carbamoyloxyethyl)) di(meth)acrylate, 1,3-di(meth)acryloyloxy-2-hydroxypropane. Combinations are possible.

Trifunctional or More Polyfunctional Monomers:

Trimethylolpropane tri(meth)acrylate, trimethylolethane tri(meth)acrylate, tetramethylolmethane tri(meth)acrylate, pentaerythritol tetra(meth)acrylate, N,N'-(2,2,4-trimethylhexamethylene)bis( 2-(aminocarboxy)-propane-1,3-diol) tetramethacrylate, 1,7-diacryloyloxy-2,2,6,6-tetraacryloyloxymethyl-4-oxyheptane. Combinations are possible.

Water (e) for use in the invention may be any one not containing impurities that may have some negative influences on the curability of the cement composition and on the bonding power of the cured product of the cement composition to teeth, for which, however, preferred is distilled water or ion-exchanged water.

The dental cement composition of the invention is characterized in that it indispensably contains additional three ingredients, (f) a peroxide, (g) a salt of an aromatic sulfinic acid, and (h) an aromatic secondary amine and/or an aromatic tertiary amine. In the dental cement composition of the invention, these three ingredients are indispensable for effectively copolymerizing the acid group-having polymerizable monomer (a) with the polymerizable monomer (d) not having an acid group in the presence of the acidic ingredients, the acid group-having polymerizable monomer (a) and the polyalkenoic acid (b).

The peroxide (f) for use in the invention includes, for example, diacyl peroxides, peroxyesters, dialkyl peroxides, peroxyketals, ketone peroxides, hydroperoxides. The diacyl peroxides include benzoyl peroxide, 2,4-dichlorobenzoyl peroxide, m-toluoyl peroxide, lauroyl peroxide. The peroxyesters include, for example, t-butylperoxy benzoate, bis-t-butylperoxy isophthalate, 2,5-dimethyl-2,5-bis(benzoylperoxy)hexane, t-butylperoxy 2-ethylhexanoate, t-butylperoxyisopropyl carbonate. The dialkyl peroxides include, for example, dicumyl peroxide, di-t-butyl peroxide. The peroxyketals include, for example, 1,1-bis(t-butylperoxy)-3,3,5-trimethylcyclohexane, 1,1-bis(t-butylperoxy)cyclohexane, 1,1-bis(t-hexylperoxy)cyclohexane. The ketone peroxides include, for example, methyl ethyl ketone peroxide, cyclohexanone peroxide, methyl acetacetate peroxide. The hydroperoxides include, for example, t-butyl hydroperoxide, cumene hydroperoxide, p-diisopropylbenzene peroxide. Combinations are possible.

The salt of an aromatic sulfinic acid (g) for use in the invention includes, for example, one or more of the lithium salts, sodium salts, potassium salts, rubidium salts, cesium salts, magnesium salts, calcium salts, strontium salts, iron salts, copper salts, zinc salts, ammonium salts, tetramethylammonium salts and tetraethylammonium salts of one or more of benzenesulfinic acid, p-toluenesulfinic acid, o-toluenesulfinic acid, ethylbenzenesulfinic acid, decylbenzenesulfinic acid, dodecylbenzenesulfinic acid, 2,4,6-trimethylbenzenesulfinic acid, 2,4,6-triisopropylbenzenesulfinic acid, chlorobenzenesulfinic acid and naphthalenesulfinic acid. Combinations are possible.

The aromatic secondary amine and/or aromatic tertiary amine (h) for use in the invention includes, for example, N-methylaniline, N-methyl-p-toluidine, N-methyl-m-toluidine, N-methyl-o-toluidine, N-ethanol-p-toluidine, N-ethanol-m-toluidine, N-ethanol-o-toluidine, ethyl p-methylaminobenzoate, ethyl m-methylaminobenzoate, ethyl o-methylaminobenzoate, p-methylaminoanisole, m-methylaminoanisole, o-methylaminoanisole, 1-methylaminonaphthalene, 2-methylaminonaphthalene, N,N-dimethylaniline, N,N-dimethyl-p-toluidine, N,N-dimethyl-m-toluidine, N,N-dimethyl-o-toluidine, N,N-diethanol-p-toluidine, N,N-diethanol-m-toluidine, N,N-diethanol-o-toluidine, ethyl p-dimethylaminobenzoate, ethyl m-dimethylaminobenzoate, ethyl o-dimethylaminobenzoate, p-dimethylaminoanisole, m-dimethylaminoanisole, o-dimethylaminoanisole, 1-dimethylaminonaphthalene and 2-dimethylaminonaphthalene. Combinations are possible.

The dental cement composition of the invention includes the acid group-having polymerizable monomer (a), the polyalkenoic acid (b), the ion-leachable glass filler (c), the polymerizable monomer (d) not having an acid group, water (e), the peroxide (f), the salt of an aromatic sulfinic acid (g), and the aromatic secondary amine and/or aromatic tertiary amine (h).

In the dental cement composition of the invention, the content of the acid group-having polymerizable monomer (a) is preferably from 0.1 to 50% by weight, more preferably from 1 to 30% by weight, based on the total weight. These ranges include all values and subranges therebetween, including 0.2, 0.5, 0.9, 1.1, 5, 10, 20, 25, 35, 40 and 45% by weight. Not only one but also two or more different types of acid group-having polymerizable monomers (a) may be in the composition. For the acid group-having polymerizable monomer (a), preferred are the polymerizable monomers of formula (I) mentioned above, and more preferred are those of formula (II) or (III) also mentioned above from the viewpoint of the bonding power of the cured product of the cement composition containing the monomer of the type. Even more preferred is combining the polymerizable monomer of formula (II) and the polymerizable monomer of formula (III) for use in the cement composition. When the polymerizable monomer of formula (II) is combined with the polymerizable monomer of formula (III) to be in the cement composition, the blend ratio of the two is not particularly limited. Preferably, however, the blend ratio (by weight) of the polymerizable monomer of formula (II)/polymerizable monomer of formula (III) falls between 0.1/99.9 and 99.9/0.1, more preferably between 1/99 and 99/1. These ranges include all values and subranges therebetween, including (for any of the numerator or denominator in the ratio) 0.5, 0.9, 2, 5, 10, 20, 30, 40, 50, 60, 70, 80, 85, 90, 95 and 99.5 as appropriate.

Preferably, the content of the polyalkenoic acid (b) in the cement composition is from 0.5 to 50% by weight, more preferably from 1 to 20% by weight. These ranges include all values and subranges therebetween, including 0.7, 1.1, 5, 10, 15, 25, 35 and 45%. Not only one but also two or more different types of polyalkenoic acids (b) may be used suitably in the composition.

The content of the ion-leachable glass filler (c) in the cement composition is preferably from 10 to 90% by weight, more preferably from 20 to 80% by weight. These ranges include all values and subranges therebetween, including 11, 15, 25, 35, 45, 55, 65 and 75%. Not only one but also two or more different types of ion-leachable glass fillers (c) may be used suitably in the composition.

The content of the polymerizable monomer (d) not having an acid group in the cement composition is preferably from 1 to 70% by weight, more preferably from 5 to 50% by weight. These ranges include all values and subranges therebtween, including 2, 10, 15, 25, 35, 45, 55 and 65%. Not only one but also two or more different types of polymerizable monomers (d) not having an acid group may be used suitably in the composition.

The content of water (e) in the cement composition is preferably from 0.5 to 50% by weight, more preferably from 2 to 30% by weight. These ranges include all values and subranges therebetween, including 0.9, 1, 5, 10, 15, 25, 35 and 45%.

The content of the peroxide (f) in the cement composition is preferably from 0.01 to 10% by weight, more preferably from 0.1 to 5% by weight. These ranges include all values and subranges therebetween, including 0.05, 0.07, 0.5, 1, 2, 3, 4, 5, 6, 7, 8 and 9%. Not only one but also two or more different types of peroxides (f) may be used suitably in the composition.

The content of the salt of an aromatic sulfinic acid (g) in the cement composition is preferably from 0.01 to 10% by weight, more preferably from 0.05 to 5% by weight. These ranges include all values and subranges therebetween, including 0.1, 0.5, 1, 2, 3, 4, 6, 7, 8 and 9%. Not only one but also two or more different types of salts of aromatic sulfinic acids (g) may be used suitably in the composition. In case where the dental cement composition of the invention is in a kit, it is desirable that the salt of an aromatic sulfinic acid (g) is packaged separately from a package containing the acid group-having polymerizable monomer (a), the polyalkenoic acid (b) and the peroxide (f).

The content of the aromatic secondary amine and/or aromatic tertiary amine (h) in the cement composition is preferably from 0.01 to 20% by weight, more preferably from 0.05 to 10% by weight. These ranges include all values and subranges therebetween, including 0.1, 0.5, 1, 2, 5, 7, 9, 11, 13, 15, 17 and 19%. Not only one but also two or more different types of aromatic secondary amines and/or aromatic tertiary amines (h) may be used suitably in the composition. In case where the dental cement composition of the invention is in a kit, it is desirable that the aromatic secondary amine and/or aromatic tertiary amine (h) is packaged separately from a package containing the peroxide (f) not to be identical component.

The dental cement composition of the invention may optionally contain a non-leachable filler. The non-leachable filler may be any of inorganic fillers, organic fillers and their composites. Combinations are possible. The inorganic fillers include, for example, silica, silica-based minerals such as kaolin, clay, mica; and silica-based ceramics and glass additionally containing any of $Al_2O_3$, $B_2O_3$, $TiO_2$, $ZrO_2$, $BaO$, $La_2O_3$, $SrO_2$, $CaO$, $P_2O_5$. Especially preferred are lanthanum glass, barium glass, strontium glass. Also usable are crystalline quartz, hydroxyapatite, alumina, titanium oxide, yttrium oxide, zirconia, barium sulfate. The organic fillers may be of organic resin, including, for example, polymethyl methacrylates, polyamides, polystyrenes, polyvinyl chlorides, chloroprene rubber, nitrile rubber, styrene-butadiene rubber. Also employable herein are inorganic/organic composite fillers, which may be prepared by dispersing a non-leachable glass filler in the organic resin, or by coating a non-leachable glass filler with the organic resin. The fillers may optionally be first surface-treated with any known surface-treating agent such as a silane coupling agent. The surface-treating agent includes, for example, vinyltrimethoxysilane, vinyltriethoxysilane, vinyltrichlorosilane, vinyltri(β-methoxyethoxy)silane, γ-methacryloylpropyltrimethoxysilane, γ-glycidoxypropyltrimethoxysilane, γ-mercaptopropyltrimethoxysilane and γ-aminopropyatriethoxysilane. Combinations are possible.

The amount of the non-leachable filler, if added in the dental cement composition of the invention, is preferably from 10 to 80% by weight, more preferably from 20 to 70% by weight. These ranges include all values and subranges therebetween, including 11, 15, 25, 35, 45, 55, 65 and 75%.

To increase the amount of the fluoride ions to be released from the dental cement composition of the invention may contain any known water-soluble fluoride compound provided that it does not negatively influence the bonding power of the cured product of the cement composition. For example, the water-soluble fluoride compound is a water-soluble metal fluoride that includes lithium fluoride, sodium fluoride, potassium fluoride, rubidium fluoride, cesium fluoride, beryllium fluoride, magnesium fluoride, calcium fluoride, strontium fluoride, barium fluoride, zinc fluoride, aluminium fluoride, manganese fluoride, copper fluoride, lead fluoride, silver fluoride, antimony fluoride, cobalt fluoride, bismuth fluoride, tin fluoride, silver diammine fluoride, sodium mono fluorophosphate, potassium titanium fluoride, fluorostannates, fluorosilicates. One or more of these may be used herein. Preferably, the metal fluoride to be added to the cement composition is ground into powder, or is coated with polysiloxane.

The dental cement composition of the invention may optionally contain any known stabilizer, photopolymerization initiator, dye, and/or pigment.

In case where the dental cement composition of the invention is in a kit, it is desirable that the constitutive ingredients are in at least two packages, for example, as in the preferred packaging embodiments (1) or (2) mentioned below from the viewpoint of the storage stability and the usability of the kit.

Packaging Embodiment (1):

This is a powder/liquid kit of the dental cement composition of the invention, in which (A) a liquid composition containing (a) an acid group-having polymerizable monomer, (b) a polyalkenoic acid, (d) a polymerizable monomer not having an acid group, (e) water and (f) a peroxide is packaged separately from (B) a powdery composition containing (c) an ion-leachable glass filler, (g) a salt of an aromatic sulfinic acid and (h) an aromatic secondary amine and/or an aromatic tertiary amine.

Packaging Embodiment (2):

This is a two-paste kit of the dental cement composition of the invention, in which (C) a paste composition containing (a) an acid group-having polymerizable monomer, (b) a polyalkenoic acid, (d) a polymerizable monomer not having an acid group, (e) water, (f) a peroxide and (i) a non-leachable filler is packaged separately from (D) a paste composition containing (c) an ion-leachable glass filler, (d) a polymerizable monomer not having an acid group, (g) a salt of an aromatic sulfinic acid and (h) an aromatic secondary amine and/or an aromatic tertiary amine.

The dental cement composition of the invention may be used, for example, as follows. In case where it is used in restoring decayed or injured teeth, the cavity of the tooth to be restored is cleaned in an ordinary manner, and the cement composition is, after being formed into a single paste, filled into the cavity of the tooth. In case where the cement composition is used in bonding prostheses, such as crowns or inlays to the cavity of a decayed or injured tooth or to an abutment, the cavity of the tooth and the surface of the prostheses are cleaned, then the cement composition is, after being formed into a single paste, applied to the tooth cavity, the abutment surface and/or the prostheses surface, and the prostheses is bonded to the tooth cavity or to the abutment surface. The dental cement composition of the invention can effectively restore decayed or injured teeth, and the restoration with it is almost complete.

EXAMPLES

Having generally described this invention, a further understanding can be obtained by reference to certain specific examples which are provided herein for purposes of illustration only and are not intended to be limiting unless otherwise specified.

Solubility and Disintegration Test Method:

A stainless mold having a diameter of 20 mm and a height of 2 mm was put on a polyethylene sheet-coated glass plate. A paste of the cement composition to be tested was cast into the mold. This was covered with a polyethylene sheet, and a glass plate was put on it and pressed against it. Nylon thread having a known weight was inserted into the mold with the cement composition therein. After the cement composition was cured, the glass plate, the polyethylene sheet and the mold were removed, and the weight of the cured cement was measured. 50 ml of 0.001 M lactic acid was put into a glass bottle with a ground-in stopper having a known weight, and two cured cements that had been prepared in the above were suspended in the bottle via the nylon thread, and kept at 37° C. for 24 hours. With that, the cured cements were taken out, and the aqueous solution in the glass bottle was dried up first at 100° C. and then at 150° C.

After cooled, the weight of the glass bottle was measured. The original weight of the glass bottle before the test was subtracted from the weight thereof after the test to obtain the weight of the evaporation residue. This indicates the degree of solubility and disintegration of the cured cement, in terms of the percentage to the original weight of the cured cement before the test.

Substances to be bonded in bonding test:

(1) Gold-Silver-Palladium Alloy:

CAST WELL MC (by GC) was cast in a size of 10 mm×10 mm×1 mm, and this is an alloy test piece to be bonded.

(2) Gold Alloy:

CASTING GOLD TYPE IV (by GC) was cast in a size of 10 mm×10 mm×1 mm, and this is another alloy test piece to be bonded.

(3) Porcelain:

One surface of a porcelain block VITA CELAY (by Vita) was smoothed by polishing it with #600-grit silicon carbide abrasive paper (by Nippon Kenshi Co. Ltd.), and make a porcelain test piece to be bonded.

(4) Composite Resin:

CLEARFILL PHOTOCURE (by Kuraray) was filled into a Teflon mold of 10 mm×10 mm×1 mm put on a smooth glass plate, covered with another glass plate, and pressed against it. With that, the resin was exposed to light from a light-curing unit, α-LIGHT II (by J. Morita Tokyo MFG Corp.) to obtain the cured resin and this makes a composite resin test piece to be bonded. Bonding Test Method:

Put into a stainless ring, the test piece was fixed in a dental composite resin therein, and its surface was polished with abrasive paper of up to #1000-grit silicon carbide (by Nippon Kenshi Co. Ltd.) with running water being applied thereto. In that manner, the surface of each test piece was smoothed. A cylindrical Teflon mold having a diameter of 4 mm and a height of 2 mm was put on the smooth surface of each test piece, and filled with a uniform paste of the cement composition to be tested. With that, the cement composition was left as it was for 30 minutes to be cured. Then, the Teflon mold was removed to release the test sample. The test sample was immersed in water at 37° C. for 24 hours. Using a universal testing machine (by Instron), the measurement of shear bond strength was made at a cross head speed of 2 mm/min. Eight test samples were prepared and tested for one cement composition, and the data were averaged to obtain the shear bond strength of the cured cement.

EXAMPLES 1, 2, AND COMPARATIVE EXAMPLES 1, 2

6-Methacryloyloxyhexyl dihydrogen phosphate (MHP) and 10-methacryloyloxydecyl dihydrogen phosphate (MDP) were used for the acid group-having polymerizable monomer (a); polyacrylic acid having a weight-average molecular weight of 25,000 was for the polyalkenoic acid (b); aluminofluorosilicate glass GM35429 (by Shott Glas) was for the ion-leachable glass filler (c); 2,2-bis(4-(3-methacryloyloxy-2-hydroxypropoxy)phenyl)propane (Bis-GMA), neopentyl glycol dimethacrylate (NPG) and 2-hydroxyethyl methacrylate (HEMA) were for the polymerizable monomer (d) not having an acid group; benzoyl peroxide (BPO) was for the peroxide (f); sodium benzenesulfinate (BSS) was for the salt of an aromatic sulfinic acid (g); and diethanol-p-toluidine (DEPT) was for the aromatic secondary amine and/or aromatic tertiary amine (h). The ingredients were blended in a ratio as in Table 1 below to prepare powder/liquid cement compositions A-1 (Example 1) and A-2 (Example 2). The cement compositions were tested for the solubility and disintegration resistance thereof and for the bond strength thereof to various adherends, according to the solubility and disintegration test method and the bonding test method mentioned above. The results are given in Table 1.

In addition, a composition B-1 (Comparative Example 1) was prepared by removing BSS from the cement composition A1 of Example 1; and a composition B-2 (Comparative Example 2) was prepared by removing BPO from the cement composition A1. These were also tested for the solubility and disintegration resistance thereof and for the bond strength thereof to various adherends, according to the test methods mentioned above. The results are given in Table 1.

The results confirm that the degree of solubility and disintegration of the dental cement compositions of the invention is significantly lower than that of the comparative compositions.

TABLE 1

| | | Example 1 (A-1) | Example 2 (A-2) | Comparative Example 1 (B-1) | Comparative Example 2 (B-2) |
|---|---|---|---|---|---|
| Liquid | MHP (wt. pts.) | 10 | — | 10 | 10 |
| | MDP (wt. pts.) | — | 10 | — | — |
| | polyacrylic acid (wt. pts.) | 30 | 30 | 30 | 30 |
| | Bis-GMA (wt. pts.) | 5 | 10 | 5 | 5 |
| | NPG (wt. pts.) | 5 | — | 5 | 5 |
| | HEMA (wt. pts.) | 10 | 10 | 10 | 10 |
| | water (wt. pts.) | 40 | 40 | 40 | 40 |
| | BPO (wt. pts.) | 1 | 1 | 1 | — |
| Powder | GM35429 (wt. pts.) | 200 | 200 | 200 | 200 |
| | BSS (wt. pts.) | 3 | 3 | — | 3 |
| | DEPT (wt. pts.) | 1 | 1 | 1 | 1 |
| Solubility and Disintegration (%) | | 0.02 | 0.04 | 0.58 | 0.42 |
| Bond Strength to gold-silver palladium alloy (MPa) | | 17.1 | 21.3 | 5.0 | 4.2 |
| Bond Strength to gold alloy (MPa) | | 16.2 | 22.6 | 6.1 | 6.7 |
| Bond Strength to porcelain (MPa) | | 15.6 | 18.0 | 3.3 | 5.4 |
| Bond Strength to composite resin (MPa) | | 14.1 | 16.2 | 3.8 | 4.2 |

Abbreviations:
MHP: 6-methacryloyloxyhexyl dihydrogen phosphate
MDP: 10-methacryloyloxydecyl dihydrogen phosphate
Bis-GMA: 2,2-bis(4-(3-methacryloyloxy-2-hydroxypropoxy)phenyl)propane
NPG: neopentyl glycol dimethacrylate
HEMA: 2-hydroxyethyl methacrylate
BPO: benzoyl peroxide
GM35429: aluminofluorosilicate glass (by Shott Glas)
BSS: sodium benzenesulfinate
DEPT: diethanol-p-toluidine

EXAMPLES 3 TO 5 AND COMPARATIVE EXAMPLES 3, 4

4-Acryloyloxybutyl dihydrogen phosphate (ABP), 10-methacryloyloxydecyl dihydrogen dithiophosphate (MDPS) and 20-methacryloyloxyeicosyl dihydrogen phosphate (MEIP) were used for the acid group-having polymerizable monomer (a); polyacrylic acid having a weight-average molecular weight of 25,000 was for the polyalkenoic acid (b); aluminofluorosilicate glass GM35429 (by Shott Glas) was for the ion-leachable glass filler (c); 2,2-bis(4-(3-methacryloyloxy-2-hydroxypropoxy)phenyl)-propane (Bis-GMA) and 2-hydroxyethyl methacrylate (HEMA) were for the polymerizable monomer (d) not having an acid group; benzoyl peroxide (BPO) was for the peroxide (f); sodium benzenesulfinate (BSS) was for the salt of an aromatic sulfinic acid (g);and diethanol-p-toluidine (DEPT) was for the aromatic secondary amine and/or aromatic tertiary amine (h). The ingredients were blended in a ratio as in Table 2 below to prepare powder/liquid cement compositions A-3 (Example 3), A-4 (Example 4) and A-5

(Example 5). The cement compositions were tested for the bond strength thereof to various adherends, according to the test method mentioned above. The results are given in Table 2.

In addition, cement compositions B-3 (Comparative Example 3) and B-4 (Comparative Example 4) were prepared as in Table 2, and these were also tested for the bond strength thereof to various adherends, according to the test method mentioned above. The results are given in Table 2.

The results confirm that the bond strength of the dental cement compositions of the invention to various adherends is high.

glycol dimethacrylate (NPG) and 2-hydroxyethyl methacrylate (HEMA) were for the polymerizable monomer (d) not having an acid group; benzoyl peroxide (BPO) was for the peroxide (f); sodium 2,4,6-triisopropylbenzenesulfinate (TPBSS) was for the salt of an aromatic sulfinic acid (g); diethanol-p-toluidine (DEPT) was for the aromatic secondary amine and/or aromatic tertiary amine (h); and a silica filler (having a mean particle size of 2.5 $\mu$m, surface-treated with 3-methacryloyloxypropyltrimethoxysilane) was for the non-leachable filler (i). The ingredients were blended in a ratio as in Table 3 below to prepare two-paste cement compositions C-1 (Example 6), C-2 (Example 7) and C-3

TABLE 2

|  |  | Example 3 (A-3) | Example 4 (A-4) | Example 5 (A-5) | Comparative Example 3 (B-3) | Comparative Example 4 (B-4) |
|---|---|---|---|---|---|---|
| Liquid | ADP (wt. pts.) | 10 | — | — | — | — |
|  | MDPS (wt. pts.) | — | 10 | — | — | — |
|  | MEIP (wt. pts.) | — | — | 10 | — | — |
|  | polyacrylic acid (wt. pts.) | 30 | 30 | 45 | 30 | 30 |
|  | Bis-GMA (wt. pts.) | 10 | 15 | — | 15 | 10 |
|  | HEMA (wt. pts.) | 10 | 15 | 10 | 15 | 10 |
|  | water (wt. pts.) | 40 | 40 | 55 | 40 | 40 |
|  | BPO (wt. pts.) | 1 | 1 | 1 | 1 | — |
| Powder | GM35429 (wt. pts.) | 200 | 200 | 200 | 200 | 200 |
|  | BSS (wt. pts.) | 3 | 3 | 3 | 3 | — |
|  | DEPT (wt. pts.) | 1 | 1 | 1 | 1 | — |
| Bond Strength to gold-silver-palladium alloy (MPa) |  | 15.3 | 24.9 | 22.5 | 3.3 | 1.1 |
| Bond Strength to gold alloy (MPa) |  | 16.0 | 25.1 | 23.8 | 4.2 | 2.0 |
| Bond Strength to porcelain (MPa) |  | 13.3 | 16.5 | 17.9 | 4.0 | 0.8 |
| Bond Strength to composite resin (MPa) |  | 12.2 | 16.8 | 17.1 | 3.1 | 1.2 |

Abbreviations:
ABP: 4-acryloyloxybutyl dihydrogen phosphate
MDPS: 10-methacryloyloxydecyl dihydrogen dithiophosphate
MEIP: 20-methacryloyloxyeicosyl dihydrogen phosphate
Bis-GMA: 2,2-bis(4-(3-methacryloyloxy-2-hydroxypropoxy)phenyl)propane
HEMA: 2-hydroxyethyl methacrylate
BPO: benzoyl peroxide
GM35429: aluminofluorosilicate glass (by Shott Glas)
BSS: sodium benzenesulfinate
DEPT: diethanol-p-toluidine

EXAMPLES 6 TO 8 AND COMPARATIVE EXAMPLES 5, 6

6-Methacryloyloxyhexyl dihydrogen phosphate (MHP), 10-methacryloyloxydecyl dihydrogen phosphate (MDP) and 20-methacryloyloxyeicosyl dihydrogen phosphate (MEIP) were used for the acid group-having polymerizable monomer (a); polyacrylic acid having a weight-average molecular weight of 25,000 was for the polyalkenoic acid (b); aluminofluorosilicate glass GM35429 (by Shott Glas) was for the ion-leachable glass filler (c); 2,2-bis(4-(3-methacryloyloxy-2-hydroxypropoxy)phenyl)-propane (Bis.-GMA), neopentyl (Example 8). The cement compositions were tested for the bond strength thereof to various adherends, according to the test method mentioned above. The results are given in Table 3.

In addition, cement compositions D-1 (Comparative Example 5) and D-2 (Comparative Example 6) were prepared as in Table 3, and these were also tested for the bond strength thereof to various adherends, according to the test method mentioned above. The results are given in Table 3.

The results confirm that the bond strength of the dental cement compositions of the invention to various adherends is high.

TABLE 3

|  |  | Example 6 (C-1) | Example 7 (C-2) | Example 8 (C-3) | Comparative Example 5 (D-1) | Comparative Example 6 (D-2) |
|---|---|---|---|---|---|---|
| Paste A | MHP (wt. pts.) | 25 | — | — | — | 20 |
|  | MDP (wt. pts.) | — | 20 | — | — | — |
|  | MEIP (wt. pts.) | — | — | 25 | — | — |
|  | polyacrylic acid (wt. pts.) | 25 | 30 | 25 | 30 | 30 |
|  | Bis-GMA (wt. pts.) | 10 | 10 | 10 | 15 | 10 |
|  | HEMA (wt. pts.) | 10 | 10 | 15 | 15 | — |
|  | water (wt. pts.) | 30 | 30 | 25 | 30 | 30 |
|  | BPO (wt. pts.) | 1 | 1 | 1 | 1 | — |
|  | silica filler (wt. pts.) | 250 | 250 | 250 | 250 | 250 |

TABLE 3-continued

|  |  | Example 6 (C-1) | Example 7 (C-2) | Example 8 (C-3) | Comparative Example 5 (D-1) | Comparative Example 6 (D-2) |
|---|---|---|---|---|---|---|
| Paste B | Bis-GMA (wt. pts.) | 40 | 40 | 40 | 40 | 40 |
|  | NPG (wt. pts.) | 40 | 40 | 40 | 40 | 40 |
|  | HEMA (wt. pts.) | 20 | 20 | 20 | 20 | 20 |
|  | GM35429 (wt. pts.) | 200 | 200 | 200 | 200 | 200 |
|  | TPBSS (wt. pts.) | 1 | 1 | 1 | 1 | — |
|  | DEPT (wt. pts.) | 1 | 1 | 1 | 1 | — |
| Bond Strength to gold-silver-palladium alloy (MPa) |  | 17.9 | 22.8 | 25.5 | 3.0 | 4.1 |
| Bond Strength to gold alloy (MPa) |  | 16.7 | 25.6 | 24.8 | 3.9 | 5.2 |
| Bond Strength to porcelain (MPa) |  | 16.3 | 19.2 | 20.0 | 3.5 | 3.0 |
| Bond Strength to composite resin (MPa) |  | 16.2 | 19.0 | 18.1 | 2.0 | 3.3 |

Abbreviations:
MHP: 6-methacryloyloxyhexyl dihydrogen phosphate
MDP: 10-methacryloyloxydecyl dihydrogen phosphate
MEIP: 20-methacryloyloxyeicosyl dihydrogen phosphate
Bis-GMA: 2,2-bis (4-(3-methacryloyloxy-2-hydroxypropoxy)phenyl)propane
HEMA: 2-hydroxyethyl methacrylate
BPO: benzoyl peroxide
NPG: neopentyl glycol Dimethacrylate
GM35429: aluminofluorosilicate glass (by Shott Glas)
TPBSS: sodium 2,4,6-triisopropylbenzensulfinate
DEPT: diethanol-p-toluidine This application is based on Japanese application JP2001-195704, filed Jun. 28, 2001, the entire contents of which are incorporated by reference.

Obviously, numerous modifications and variations of the present invention are possible in light of the above teachings. It is therefore to be understood that within the scope of the appended claims, the invention may be practiced otherwise than as specifically described herein.

What is claimed is:

1. A dental cement composition, comprising:
(a) an acid group-having polymerizable monomer,
(b) a polyalkenoic acid,
(c) an ion-leachable glass filler,
(d) a polymerizable monomer not having an acid group,
(e) water,
(f) a peroxide,
(g) a salt of an aromatic sulfinic acid, and
(h) at least one compound selected from the group consisting of an aromatic secondary amine, an aromatic tertiary amine, and a combination thereof.

2. The dental cement composition according to claim 1, wherein the content of the acid group-having polymerizable monomer (a) ranges from 0.1 to 50% by weight.

3. The dental cement composition according to claim 1, wherein the content of the polyalkenoic acid (b) ranges from 0.5 to 50% by weight.

4. The dental cement composition according to claim 1, wherein the content of the ion-leachable glass filler (c) ranges from 10 to 90% by weight.

5. The dental cement composition according to claim 1, wherein the content of the polymerizable monomer (d) not having an acid group ranges from 1 to 70% by weight.

6. The dental cement composition according to claim 1, wherein the content of water (e) ranges from 0.5 to 50% by weight.

7. The dental cement composition according to claim 1, wherein the content of the peroxide (f) ranges from 0.01 to 10% by weight.

8. The dental cement composition according to claim 1, wherein the content of the salt of an aromatic sulfinic acid (g) ranges from 0.01 to 10% by weight.

9. The dental cement composition according to claim 1, wherein the content of at least one amine compound selected from the group consisting of the aromatic secondary amine, the aromatic tertiary amine and combinations thereof (h) ranges from 0.01 to 20% by weight.

10. The dental cement composition according to claim 1, wherein the aromatic secondary amine and/or aromatic tertiary amine is at least one compound selected from the group consisting of N-methylaniline, N-methyl-p-toluidine, N-methyl-m-toluidine, N-methyl-o-toluidine, N-ethanol-p-toluidine, N-ethanol-m-toluidine, N-ethanol-o-toluidine, ethyl p-methylaminobenzoate, ethyl m-methylaminobenzoate, ethyl o-methylaminobenzoate, p-methylaminoanisole, m-methylaminoanisole, o-methylaminoanisole, 1-methylaminonaphthalene, 2-methylaminonaphthalene, N,N-dimethylaniline, N,N-dimethyl-p-toluidine, N,N-dimethyl-m-toluidine, N,N-dimethyl-o-toluidine, N,N-diethanol-p-toluidine, N,N-diethanol-m-toluidine, N,N-diethanol-o-toluidine, ethyl p-dimethylaminobenzoate, ethyl m-dimethylaminobenzoate, ethyl o-dimethylaminobenzoate, p-dimethylaminoanisole, m-dimethylaminoanisole, o-dimethylaminoanisole, 1-dimethylaminonaphthalene and 2-dimethylaminonaphthalene.

11. The dental cement composition according to claim 1, wherein the salt of an aromatic sulfinic acid (g) is a lithium, sodium, potassium, rubidium, cesium, magnesium, calcium, strontium, iron, copper, zinc, ammonium, tetramethylammonium, or tetraethylammonium salt of at least one aromatic sulfinic acid selected from the group consisting of benzenesulfinic acid, p-toluenesulfinic acid, o-toluenesulfinic acid, ethylbenzenesulfinic acid, decylbenzenesulfinic acid, dodecylbenzenesulfinic acid, 2,4,6-trimethylbenzenesulfinic acid, 2,4,6-triisopropylbenzenesulfinic acid, chlorobenzenesulfinic acid and naphthalenesulfinic acid.

12. The dental cement composition according to claim 1, wherein the ion-leachable glass filler is at least one member selected from the group consisting of fluoroaluminosilicate glass, calcium fluoroaluminosilicate glass, strontium fluoroaluminosilicate glass, barium fluoroaluminosilicate glass and strontium calcium fluoroaluminosilicate glass.

13. The dental cement composition according to claim 1, wherein the acid group-having polymerizable monomer is a member selected from the group consisting of 2-(meth) acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth) acryloyloxyundecyl dihydrogen phosphate, 12-(meth) acryloyloxydodecyl dihydrogen phosphate, 16-(meth) acryloyloxyhexadecyl dihydrogen phosphate, 20-(meth) acryloyloxyeicosyl dihydrogen phosphate, di(2-(meth) acryloyloxyethyl hydrogen phosphate, di(4-(meth) acryloyloxybutyl hydrogen phosphate, di(6-(meth) acryloyloxyhexyl hydrogen phosphate, di(8-(meth) acryloyloxyoctyl hydrogen phosphate, di(9-(meth) acryloyloxynonyl hydrogen phosphate, di(10-(meth) acryloyloxydecyl hydrogen phosphate, 1,3-di(meth) acryloyloxypropyl-2-dihydrogen phosphate, 2-(meth) acryloyloxyethyl phenyl hydrogen phosphate, 2-(meth) acryloyloxyethyl-2'-bromoethyl hydrogen phosphate, 2-(meth)acryloyloxyethyl phenyl phosphonate, (5-methacryloxy)pentyl-3-phosphonopropionate, (6-methacryloxy) hexyl-3-phosphonopropionate, (10-methacryloxy)decyl-3-phosphonopropionate, (6-methacryloxy)hexyl-3-phosphonoacetate, (10methacryloxy)decyl-3-phosphonoacetate, 2-methacryloyloxyethyl-4-methoxyphenyl hydrogen phosphate, 2-methacryloyloxypropyl-4-ethoxyphenyl hydrogen phosphate, glycerol phosphate di(meth)acrylate, dipentaerythritol phosphate penta(meth)acrylate and their acid chlorides.

14. The dental cement composition according to claim 1, wherein the content of the acid group-having polymerizable monomer (a) ranges from 0.1 to 50% by weight, the content of the polyalkenoic acid (b) ranges from 0.5 to 50% by weight, the content of the polyalkenoic acid (b) ranges from 0.5 to 50% by weight, the content of the ion-leachable glass filler (c) ranges from 10 to 90% by weight, the content of the polymerizable monomer (d) not having an acid group ranges from 1 to 70% by weight, the content of water (e) ranges from 0.5 to 50% by weight, the content of peroxide (f) ranges from 0.01 to 10% by weight, the content of the salt of an aromatic sulfinic acid (g) ranges from 0.01 to 10% by weight, and the content of the aromatic secondary amine and/or aromatic tertiary amine (h) ranges from 0.01 to 20% by weight.

15. The dental cement composition according to claim 1, wherein the acid group-having polymerizable monomer (a) is a polymerizable monomer having the following formula (I):

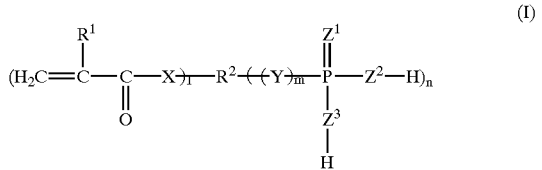

wherein $R^1$ represents a hydrogen atom or a methyl group;
$R^2$ represents an organic group having from 2 to 40 carbon atoms;
X represents a group of —O— or NH—;
l indicates an integer ranging from 1 to 5;
m indicates an integer 0 or 1;
n indicates an integer ranging from 1 to 4;

Y represents a group of —O— or —S—; and
$Z^1$, $Z^2$ and $Z^3$ each independently represent an oxygen atom or a sulfur atom.

16. The dental cement composition according to claim 1, wherein the acid group-having polymerizable monomer (a) is a polymerizable monomer having the following formula (II) or (III):

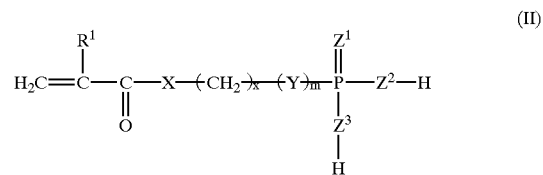

wherein $R^1$ represents a hydrogen atom or a methyl group;
X represents a group of —O— or —NH—;
x indicates an integer ranging from 4 to 20;
m indicates an integer 0 or 1;
Y represents a group of —O— or —S—; and
$Z^1$, $Z^2$ and $Z^3$ each independently represent an oxygen atom or a sulfur atom;

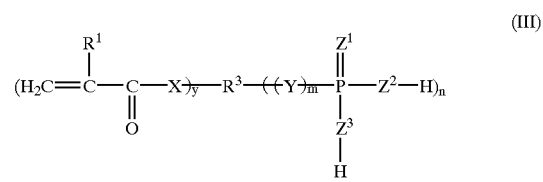

wherein $R^1$ represents a hydrogen atom or a methyl group;
$R^3$ represents an organic group having from 3 to 10 carbon atoms;
X represents a group of —O— or —NH—;
y indicates an integer ranging from 2 to 5;
m indicates an integer 0 or 1;
n indicates an integer ranging from 1 to 4;
Y represents a group of —O— or —S—; and
$Z^1$, $Z^2$ and $Z^3$ each independently represent an oxygen atom or a sulfur atom.

17. A dental cement composition kit, which comprises:
(A) a liquid composition, comprising:
(a) an acid group-having polymerizable monomer,
(b) a polyalkenoic acid,
(d) a polymerizable monomer not having an acid group,
(e) water, and
(f) a peroxide, and
(B) a powdery composition, comprising:
(c) an ion-leachable glass filler,
(g) a salt of an aromatic sulfinic acid, and
(h) at least one compound selected from the group consisting of an aromatic secondary amine, an aromatic tertiary amine, and a combination thereof, wherein (A) and (B) are packaged separately from each other.

18. A dental cement composition kit, which comprises:
(C) a paste composition, comprising:
(a) an acid group-having polymerizable monomer,
(b) a polyalkenoic acid,
(d) a polymerizable monomer not having an acid group,
(e) water, and
(f) a peroxide,
(i) a non-leachable filler; and (D) a paste composition, comprising:
  (c) an ion-leachable glass filler,
  (d) a polymerizable monomer not having an acid group,
  (g) a salt of an aromatic sulfinic acid, and
  (h) at least one compound selected from the group consisting of an aromatic secondary amine, an aromatic tertiary amine, and a combination thereof, wherein (C) and (D) are packaged separately from each other.

19. A method for making a dental cement, comprising: contacting the following components (a) to (h) and curing:
  (a) an acid group-having polymerizable monomer,
  (b) a polyalkenoic acid,
  (c) an ion-leachable glass filler,
  (d) a polymerizable monomer not having an acid group,
  (e) water,
  (f) a peroxide,
  (g) a salt of an aromatic sulfinic acid, and
  (h) at least one compound selected from the group consisting of an aromatic secondary amine, an aromatic tertiary amine, and a combination thereof.

20. A method, comprising: introducing the composition of claim 1 into the oral cavity of a subject.

21. A method, comprising:
contacting the composition according to claim 1 with at least one member selected from the group consisting of hard tissue, tooth enamel, dentin, prosthesis, inlay, onlay, crown, core, post, bridge, metal, porcelain, ceramic, composite resin and combinations thereof.

22. A dental cement, comprising:
a cured product of the composition according to claim 1.

23. A dental appliance or article, comprising:
a cured product of the composition according to claim 1 in contact with at least one member selected from the group consisting of hard tissue, tooth enamel, dentin, prosthesis, inlay, onlay, crown, core, post, bridge, metal, porcelain, ceramic, composite resin and combinations thereof.

24. A method for making a dental cement, comprising:
combining components (A) and (B) as claimed in claim 17 into a single material.

25. A method, comprising:
introducing components (A) and (B) as claimed in claim 17 or a mixture thereof, into the oral cavity of a subject.

26. A method, comprising:
contacting components (A) and (B) as claimed in claim 17 or a mixture thereof, with at least one member selected from the group consisting of hard tissue, tooth enamel, dentin, prosthesis, inlay, onlay, crown, core, post, bridge, metal, porcelain, ceramic, composite resin and combinations thereof.

27. A dental cement, comprising:
a cured product of components (A) and (B) as claimed in claim 17.

28. A dental appliance or article, comprising:
a cured product of the components (A) and (B) of claim 17 in contact with at least one member selected from the group consisting of hard tissue, tooth enamel, dentin, prosthesis, inlay, onlay, crown, core, post, bridge, metal, porcelain, ceramic, composite resin and combinations thereof.

29. A method for making a dental cement, comprising:
combining components (C) and (D) as claimed in claim 18.

30. A method, comprising:
introducing components (C) and (D) as claimed in claim 18 or a mixture thereof, into the oral cavity of a subject.

31. A method, comprising:
contacting components (C) and (D) as claimed in claim 18 or a mixture thereof, with at least one member selected from the group consisting of hard tissue, tooth enamel, dentin, prosthesis, inlay, onlay, crown, core, post, bridge, metal, porcelain, ceramic, composite resin and combinations thereof.

32. A dental cement, comprising:
a cured product of components (C) and (D) as claimed in claim 18.

33. A dental appliance or article, comprising:
a cured product of the components (C) and (D) as claimed in claim 18 in contact with at least one member selected from the group consisting of hard tissue, tooth enamel, dentin, prosthesis, inlay, onlay, crown, core, post, bridge, metal, porcelain, ceramic, composite resin and combinations thereof.

* * * * *